United States Patent [19]
Ort

[11] 3,981,800
[45] Sept. 21, 1976

[54] HIGH QUALITY METHANE GAS THROUGH MODIFIED ANAEROBIC DIGESTION

[75] Inventor: Jay E. Ort, Lewistown, Pa.

[73] Assignee: ERA, Incorporated, Clovis, N. Mex.

[22] Filed: Nov. 22, 1974

[21] Appl. No.: 526,176

[52] U.S. Cl. .................................. 210/6; 210/12; 210/16; 195/27
[51] Int. Cl.² ......................................... C02C 1/14
[58] Field of Search ................. 210/2, 4, 5, 6, 10, 210/12, 14, 16, 180, 3; 195/1, 28 R, 104, 108, 27; 48/209, 197 A

[56] References Cited
UNITED STATES PATENTS

| | | | |
|---|---|---|---|
| 663,623 | 12/1900 | Cameron | 195/27 |
| 1,420,250 | 6/1922 | Gavett | 210/2 |
| 3,640,846 | 2/1972 | Johnson | 48/209 |
| 3,687,646 | 8/1972 | Brent | 48/209 |
| 3,838,199 | 9/1974 | Coe et al. | 210/2 |
| 3,890,113 | 6/1975 | Child | 48/209 |

Primary Examiner—Charles N. Hart
Assistant Examiner—Ernest G. Therkorn
Attorney, Agent, or Firm—Berman, Aisenberg & Platt

[57] ABSTRACT

Conventional anaerobic digestion, as practiced in municipal waste treatment plants, is modified to yield high-quality methane gas. Upwards of 98 percent methane is produced rather than the normal 60 to 70 percent methane (diluted with carbon dioxide).

The process, wherein digestion is conducted under several atmospheres of pressure, involves the application of Henry's Law. Digesting sludge is used as a scrubbing agent. According to one system a recirculation loop features pressure release and degassing of carbon dioxide. Degassed sludge is then pumped, under pressure, back into a digestion tank. The recirculation rate is designed to maintain sludge in the digester in an unsaturated state with regard to carbon dioxide solubility. This keeps the carbon dioxide from precipitating out of the sludge within the digestion tank and results in high purity methane production. Another system accomplishes similar results by periodically depressurizing the digestion tanks to allow carbon dioxide to escape. This configuration requires no recirculation for degassification.

17 Claims, 3 Drawing Figures

HIGH QUALITY METHANE GAS THROUGH MODIFIED ANAEROBIC DIGESTION

BACKGROUND

In recent times a world-wide energy shortage has prompted a search for non-fossil sources of energy. One obvious alternate source of energy is the production of methane gas through anaerobic digestion of organic solid wastes. Methane gas has been produced from the digestion of sewage sludge for at least 50 years in both Europe and United States. Methane has also been produced from animal wastes and used for running automobile engines and heating homes as well as for running engines and compressors at sewage plants. Thus-produced methane has two important impediments to full utilization: (1) it contains 30 to 40 percent carbon dioxide, which reduces its heating value to about 600 BTU's per cubic foot (compared to 1000 BTU natural gas), and (2) it also normally contains a small amount of hydrogen sulfide which makes it highly corrosive. The corrosive element makes the gas usable only in specifically-designed more expensive engines and makes it unsuitable for blending with pipeline-quality natural gas.

To make the gas fully compatible with pipeline gas or usable in standard engines, it may be scrubbed. There are a number of commercial processes available for removing acid gases ($CO_2$ and $H_2S$), but they are all relatively expensive. Also, they do not lend themselves well to scrubbing the relatively small quantities of gas which might be produced from organic solid wastes from cities or even the wastes from a large beef cattle feedlot operation.

SUMMARY OF THE INVENTION

The basic system employs (a) digestion of solid wastes at a temperature of approximately 95°F (35°C), (b) mixing the contents of digesters and (c) recirculating sludge to provide seed and favorable population dynamics. All of these practices improve digestion efficiency and decrease to about 10 days the time required to achieve complete digestion.

Whereas conventional anaerobic digestion is effected under a pressure of at most only a few inches of water, the present digestion is conducted under a pressure of from 2 to 5 atmospheres (approximately 30 to 75 psig). For above-ground operations digestion tanks operated at such pressures are economically constructed of steel. Alternatively-employed underground digestion tanks can be made of other material. Pressurization by use of a hydrostatic head is readily employed for underground digestion tanks (digesters).

Henry's Law indicates that the solubility of a gas is directly proportional to pressure. For instance, at 30°C and standard atmospheric pressure, the solubility of carbon dioxide in water is 655 milliliters per liter (ml/l), and that of methane is 27.6 ml/l. If the pressure is increased by one atmosphere, solubility of both gases is doubled. Each additional atmosphere of pressure adds 665 milliliters of solubility to a carbon dioxidewater system at 30°C. In typical digestion practice a pressure of 5 atmospheres gauge would increase solubility of carbon dioxide and methane to yield a gas with 66 to 68 percent methane. A pressure of nearly 20 atmospheres gauge would be required to yield nearly pure methane. In addition to pressure, the volume of water is an important variable in such a system. A large water volume entails large tanks and high tanks; dilution is detrimental to population dynamics and high energy costs (for heating the water to 35°C). To provide a large effective volume of water without these problems, recirculation is used. By combining a pressure of from 2 to 5 atmospheres gauge with a recirculation rate of from 4 to 10 times the daily feed volume, high quality methane is produced efficiently as little additional construction or operating cost, compared to conventional practice. Alternatively, digestion tanks are periodically depressurized; this, too, results in an increase in effective volume for carbon dioxide absorption.

In modern digesters which use external sludge heating units, approximately two to four times the feed volume is circulated through the sludge heater daily. This makes adaptation of a carbon dioxide stripping unit very simple. On this same recirculation loop at 5 atmospheres (gauge), the entire sludge flow, after heating, may be degassed. This heating (normally about 6°C) decreases carbon dioxide solubility approximately 13 percent and improves degassification efficiency. When the digesters are operated at lower pressures, a greater recirculation volume is required and only a portion of the degassing loop is heated.

After degassing, either by mixing, sheet flow, and/or bubbling warm gas (optionally from a compressor exhaust through the sludge), a pump repressurizes the sludge back into the stage one digester (withdrawal is from the stage 2 digester as shown in FIG. 1). In effect, the operation consists of withdrawing nearly saturated (with respect to carbon dioxide at operating temperature and pressure) sludge from stage 2, heating at least part of the flow, degassing and then reintroducing the unsaturated sludge into the stage 1 digester. This maintains the sludge within the digesters in an unsaturated state and essentially all carbon dioxide, as well as hydrogen sulfide, is kept in solution in the sludge. Even under pressure and recirculation, no more than four percent of all methane generated remains in solution and is subject to loss during degassing.

If in-tank degassing is used, a reduction in pressure to atmospheric is required for 15 to 20 minutes periodically. Frequency of degassing depends upon operating pressure. Higher pressures require less frequent depressurization.

By subjecting relatively conventional digestion to a pressure of from 2 to 5 atmospheres (gauge) and incorporating pressurized recirculation in a practical application of Henry's Law, relatively pure methane gas is produced without incurring scrubbing costs. In effect scrubbing is accomplished internally; it requires digesters which are designed to operate at the noted superatmospheric pressures, but such does not greatly add to either construction or operation cost as would scrubbing.

According to conventional digestion practices a large part of the operating cost is for transporting manure feedstock to a central location. Scrubbing equipment used in the natural gas industry is essentially designed for relatively large operations which require establishing a large centralized facility. By comparison, the present invention, which accomplishes scrubbing "internally", is economically feasible on any cattle feedlot with a capacity of at least 10,000 head without any hauling other than that required for ordinary routine pen clean-up.

The primary aspect of the subject invention is the anaerobic digestion of organic solid waste, e.g. manure, to produce methane gas. More particularly, the invention concerns producing high-quality methane gas, e.g. that of about 98 percent or higher purity, by conducting such anaerobic digestion under superatmospheric pressure, e.g. a pressure of at least about one atmosphere gauge and preferably from about 2 to about 5 atmospheres gauge.

Such pressurized anaerobic digestion increases carbon dioxide availability as a hydrogen acceptor for biological methane gas formation. When anaerobic digestion is effected under the contemplated pressure, release of the pressure facilitates flotation thickening of thus-produced digested sludge. Depressurizing sludge which has been digested under pressure and then recirculating it for further digestion under pressure strips or scrubs from the digested sludge acid gases, such as carbon dioxide and hydrogen sulfide, formed in and along with the sludge during digestion. Such stripping or scrubbing increases the quality of methane gas produced. The acid gases are also removed during digestion, if desired, by relieving the pressure temporarily, e.g. by venting, either once or at intervals.

Recirculation of depressurized sludge back to pressurized digestion results in maintaining digesting sludge in an unsaturated state with regard to carbon dioxide concentration. Heating temporarily-depressurized sludge improves the process efficiency of subsequent gas-stripping and the entire process when the resulting stripped sludge is recirculated for further pressurized digestion.

Anaerobic pressurized digestion of organic solid waste, e.g. manure, with recirculation of depressurized sludge yields about 0.5 pound of sludge (90 percent by weight or higher solids) and in excess of about 3.5 cubic feet (at a pressure of 800 psig) of high-quality (at least about 98 percent purity) methane gas per pound of organic solid-waste feed even when some of the produced methane gas has been used for heating recirculating sludge, for drying dewatered (35 to 45 percent by weight solids) sludge and for compressing produced methane gas from a pressure of 36 psig to 800 psig.

An object of this invention is to produce methane gas of a purity sufficient for its practical use as fuel. Another object is to obtain such purity without conventional scrubbing equipment. Objects include producing high-purity methane gas economically, producing it without extensive hauling and without an unduly large operation. A further object is to make only a minimal modification of conventional anaerobic sludge digestion systems for such high-purity methane gas. A still further object is to attain highpurity methane gas by conducting anaerobic organic-waste digestion at superatmospheric pressure and with recirculation of obtained digested sludge. Other objects are apparent from the subject disclosure.

DETAILED DESCRIPTION OF DRAWINGS

Although the drawings are only illustrative of species of the subject invention and are in no way limitative, a detailed description is provided of exemplary component equipment and material flow to assist with a complete understanding of working embodiments.

Figure 1:
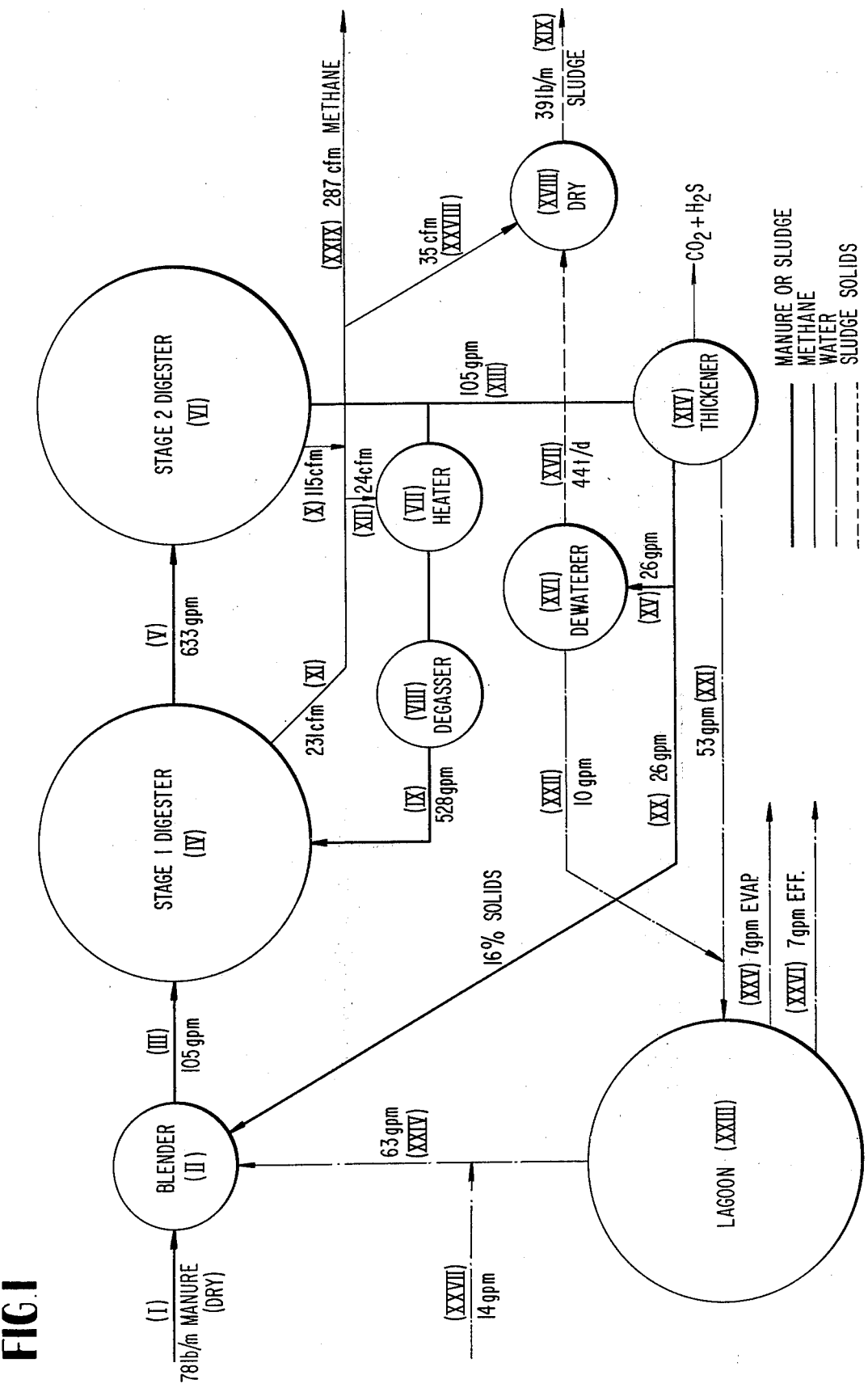
FIG. 1 is a schematic representation of a system designed for anaerobic digestion of sludge (with mechanical degassing and recirculation) to produce 0.4 million cubic feet of methane gas per day.

With reference to the configuration represented in FIG. 1, operative parameters are indicated in Table I.

TABLE I

| | | | FIG. 1 DETAILS | | |
|---|---|---|---|---|---|
| | Component | Residence Time | Temp. (°F) | Pressure (psig) | Function |
| II | Blender | 15 minutes | 60–80 | ambient | Blends 78 pounds per minute (lb/m) of dry* manure (I), 63 gallons per minute (gpm) of water (XXIV) and 26 gpm of seed sludge (XX) to about 12 percent solids |
| IV | Digester Stage 1 | 5 days (average) | 94–96 | 36–45 | Bacterial action on 105 gpm of blended manure and digested sludge (III) and on 528 gpm of degassed digested sludge (IX) progressively converts organic solids to organic acids and methane and bacterial cells (aided by heating, mixing and seed) - yields 231 cubic feet**° per minute (cfm) of methane gas (XI) at about 36 psig |
| VI | Digester Stage 2 | 5 days (average) | 93–95 | 36–45 | Bacterial action on 633 gpm of partially-digested sludge (V) goes to virtual completion (aided by heating, mixing and recirculation) - yields 115 cfm (X) of methane gas [the effective total yield*** is 287 cfm (XXIX) of methane gas (from IV and VI) at about 36 psig, of which 9 cfm is sufficient to compress it (in a suitable |

TABLE I-continued

FIG. 1 DETAILS

| | Component | Residence Time | Temp. (°F) | Pressure (psig) | Function |
|---|---|---|---|---|---|
| | | | | | compressor) to gas-line pressure] and 633 gpm of digested sludge |
| VII | Heater | less than 5 minutes | 103–105 | 36–45 | 24 cfm of produced methane gas (XII) is used to heat a portion of recirculated sludge (IX) to maintain digester (IV) at 95°F |
| VIII | Degasser | less than 5 minutes | 93–98 | ambient | Strips supersaturated $CO_2$ and $H_2S$ from sludge by exposure to air |
| XIV | Thickener | 20 minutes | 90–95 | ambient | Concentrates 105 gpm of digested sludge (XIII) [from about 8% solids to about 16% solids] by dissolved-air-flotation thickening to yield 52 gpm of concentrated sludge and 53 gpm of water (XXI) |
| XVI | Dewaterer | 12 minutes (average) | 87–92 | ambient | Further concentrates sludge solids from 26 gpm of thickened sludge (XV) by filtration and wringer device to yield 44 tons per day (t/d) of dewatered sludge XVII (from 35–45 percent solids) and 10 gpm of water XXII |
| XVIII | Drier | 6 minutes (average) | 220–225 | ambient | Uses 35 cfm of produced methane gas (XXVIII) to yield 39 pounds per minute (lb/m) of dry (having at most 10 percent moisture) sludge (XIX) from 44 t/d of dewatered sludge XVII |
| XXIII | Lagoon | 20 days | 40–80 | ambient | From 53 gpm of thickener water (XXI) and 10 gpm of dewaterer water (XXII) controls ammonia level of recycle water [49 gpm to (II)], reduces organics in waste-water effluent [7 gpm (XXVI)] and loses about 7 gpm of water (XXV) by evaporation [effluent water and evaporation loss are replaced by 14 gpm** of water XXVII] |

Note:
*The 78 pounds indicates the weight of solids; the manure feed may actually range from 20 to 80 percent moisture.
An average figure of 14 gpm is required but will vary with process losses, including evaporation rate from the lagoon. In very wet weather makeup may be as little as 7 gpm; in very dry weather over 20 gpm may be required. That water along with recycle water from the lagoon enters the process at the blender.*Stage 1 and Stage 2 Digesters yield 346 [231 + 115] cfm of methane gas, approximately 230 cfm of carbon dioxide and about 3 cfm of hydrogen sulfide.
***All cmf figures throughout the specification and drawings reflect measurements under normal temperature and pressure (NTP) conditions, i.e. at 760 mm Hg (atmospheric pressure) and 0°C (32°F).

Figure 2:
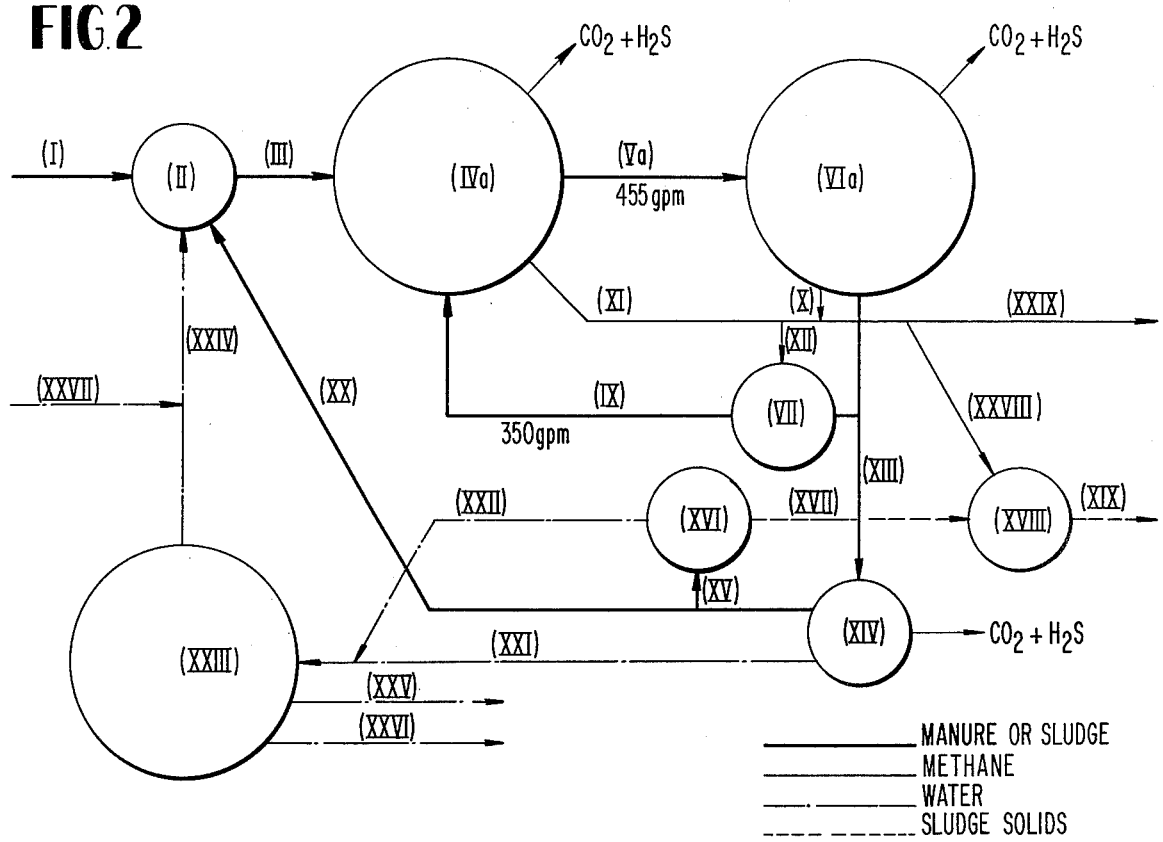
FIG. 2 is a schematic representation of an alternative system designed for anaerobic digestion of sludge (with underground digesters under hydrostatically-impressed superatmospheric pressure) to produce 0.4 million cubic feet per day (cfd) of methane gas.

With reference to the configuration represented in FIG. 2, operative parameters (insofar as they differ from those indicated in the detailed description of FIG. 1) are presented in Table II.

TABLE II

FIG. 2 DETAILS

| | Component | Residence Time | Temp. (°F.) | Pressure (psig) | Function |
|---|---|---|---|---|---|
| IVa | Digester Stage 1 | 5 days (average) | 94–96 | 36–45 | Constructed underground with a hydrostatic head; $CO_2$ and $H_2S$ are vented; bacterial action is the same as that for digester IV, but only 455 gpm of partially digested sludge (Va) are transmitted to digester VIa and only 350 gpm of digested and heated sludge IX are recirculated to this unit |
| VIa | Digester Stage 2 | 5 days (average) | 93–95 | 36–45 | Constructed underground with a hydrostatic head; $CO_2$ and $H_2S$ are vented; bacterial action is the |

TABLE II-continued

FIG. 2 DETAILS

Figure 3:
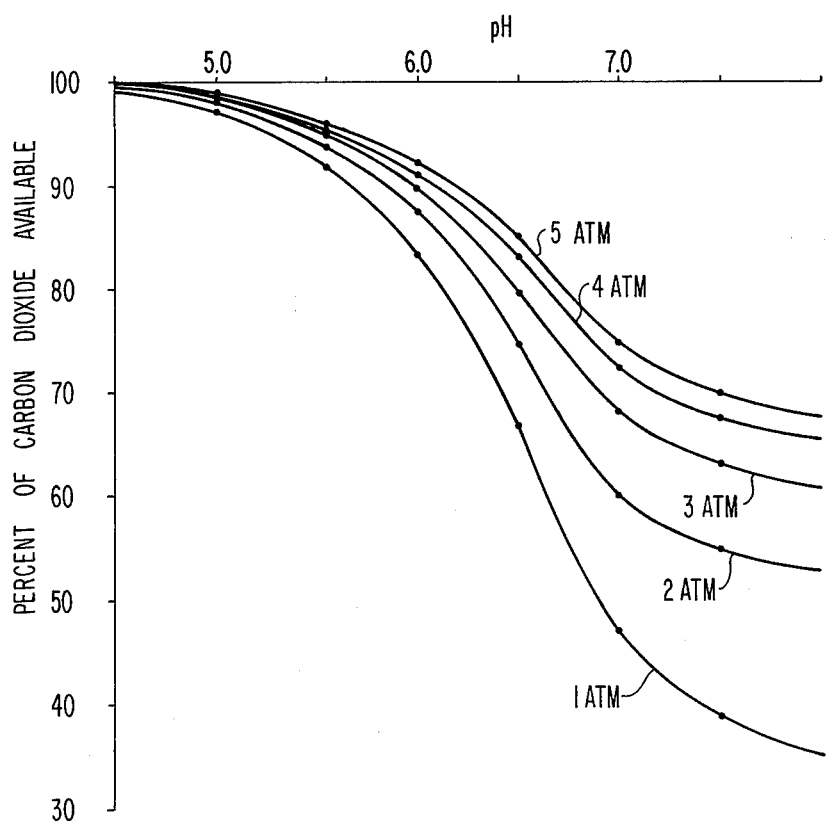
FIG. 3 is a graph which shows the effect of pH and pressure on degassing efficiency.

| | Component | Residence Time | Temp. (°F.) | Pressure (psig) | Function |
|---|---|---|---|---|---|
| XIV | Thickener | 20 minutes | 90–95 | ambient | same as that for digester VI, but only 455 gpm of digested sludge [(IX) plus (XIII)] are produced Thickening is effected in the same manner as described with regard to FIG. 1; a small amount (less than 15 percent by volume) of produced $CO_2$ and $H_2S$ are vented during thickening | pH has a considerable bearing upon how closely carbon dioxide solubility follows Henry's Law. At atmospheric pressure and the temperature under consideration, virtually all carbon dioxide forms carbonic acid at a pH of less than 3.8. In this form (carbonic acid) the carbon dioxide is readily available for scrubbing because of the reversible nature of carbonic acid formation. As the pH is raised above 3.8 an increasing percentage of the carbon dioxide (which has dissolved to form carbonic acid) ionizes to form the bicarbonate radical. This reaction is not reversible at a given pH, and the carbon dioxide in this form cannot be degassed. Therefore, as the pH moves upward, solubility and degassing progressively deviate from following Henry's Law. In addition, as pressure is increased, solubility and degassing more closely conform to Henry's Law. FIG. 3 illustrates precisely how degassing efficiency is affected by pH and pressure. From this graph efficiency factors for various pressures can be extracted.

Because digesters operate best in a pH range of 6.3 to 6.8, an efficiency factor of 75 to 85 percent prevails at from 2 to 5 atmospheres.

An operational option is to acidify the degassing loop just ahead of the degasser. Then, after degassing, ammonium hydroxide (which could enhance sludge value) or other alkaline material is used to adjust the pH upward prior to being recirculated into the digesters. Because of the buffering capacity of the sludge, this option is not presently economically attractive. Efficiency in the 80 percent range is not particularly uneconomical and is attained without pH manipulation.

EXEMPLARY EQUIPMENT

For installations, e.g., of the type depicted by FIGS. 1 and 2 over-all size, and thus size of each respective piece of equipment, is dependent upon economic feasibility, which is ultimately based on the market value of produced methane gas and produced dry sludge. At current values [upwards of 1 dollar per cubic foot for methane gas and 25 dollars or more per ton for dry sludge] units which yield as little as 200,000 cubic feet per day are feasible. Upper limits on size are essentially non-existant. Assuming efficient operation of the degasser (FIG. 1), the purity of produced methane is in excess of 98 percent and as high as 99.7 percent methane.

For the installations shown in FIGS. 1 and 2, typical equipment is:

II. Blender — Infilco Vorti-mixer unit, 2 horsepower (HP) with turbulent mix, at ambient atmospheric pressure and temperature dependent upon the constituents to be blended, namely: (1) recycle water generally between 50° and 80° F, (2) make-up water normally between 60° and 65° F, (3) recycle thickened sludge at 95° F and (4) manure with a temperature of from 50° to 80° F, seasonally. On this basis the blender contents range between approximately 60° F(15°C) and 80° F (28°C). Residence time for all ingredients is approximately 15 minutes. Basin and mixer specifications are proportionally sized for larger or smaller operations.

IV. Stage 1 Digester — 34 feet side-wall height, 50 feet in diameter, cylindrical steel tank with hemispherical dome and 20° cone bottom, equipped with 5 HP mixing system (gentle mixing) equal to Dorr-Oliver Dynamix or Infilco Vorti-mix units. Tank should be rated for 45 psig working pressure, cylindrical wall area should be built below grade to facilitate pressure containment. One such unit required.

VI. Stage 2 Digester [Identical to Stage 1 digester.] One such unit required.

VII. Heater — Rexnord (formerly PFT) Model 2006 sludge heater. Two million BTU per hour rating or equivalent. One such unit required.

VIII. Degasser — Infilco Multicone Aerator of 600 gpm capacity. One such unit required.

XIV. Thickener — Permutit Favair Mark II OB 30 — 5 HP Air-Water Flotation Thickener of nominal 150 gpm capacity. One such unit required.

XVI. Dewaterer — Standard Model Smith and Loveless sludge concentrator. Five such units required.

XVIII. Drier-Heil Model SD 75-22, 2,000 to 6,000 pounds of water per hour. One such unit required.

XXIII. Lagoon — 1.5 surface acres grading from 6 feet in depth at inlet to 2 feet in depth at outlet end and 3:1 length-to-width ratio. One such unit required.

Each of the preceding units of equipment (other than the digesters and lagoon) is a shelf item. When the digesters are hydrostatically pressurized (as in FIG. 2), the standpipe contains less than 2 percent of the digester volume and is outside of the zone of mixing so that no significant watering-down is effected.

The above-noted equipment is sized for operations designed to produce 0.4 million cubic feet [NTP] per day of high-quality, i.e. at least 98 percent, methane gas at pipe-line pressure. Feed rate and equipment size are correspondingly geared to desired plant capacity, which can vary over a considerable range. Neither feed rate, equipment size not plant capacity is a critical factor, per se, of the subject invention.

RELATED CONSIDERATIONS

Assuming that an anaerobic digestion process (high-rate), operated at atmospheric pressure, produces a gas of 60 percent methane and 40 percent carbon dioxide, the values shown in Table III can be projected for the same system under the indicated pressures. As the table shows, essentially pure methane should result at 294 psig.

TABLE III

EQUILIBRIUM METHANE CONTENT AT PRESSURE

| Pressure (psig) | Methane % | Absorption Coefficient |
| --- | --- | --- |
| 0 | 60.0 | 0 |
| 14.7 | 61.3 | 1 |
| 29.4 | 62.6 | 2 |
| 44.1 | 64.0 | 3 |
| 58.8 | 65.6 | 4 |
| 88.2 | 68.3 | 6 |
| 117.6 | 72.3 | 8 |
| 147.0 | 76.3 | 10 |
| 176.4 | 80.7 | 12 |
| 205.8 | 85.7 | 14 |
| 235.2 | 91.5 | 16 |
| 264.6 | 98.1 | 18 |
| 294.0 | 100.0 | 20 |

The adsorption coefficient of sludge is somewhat different from that of water, upon which Table III is based. Sewage and sewage sludge are normally considered to have a coefficient of absorption of 90 to 95 percent that of water. Gas production is dependent upon the activity of two general classes, i.e. acid-forming and methane-forming, of bacteria. Although carbon dioxide is used as a hydrogen acceptor in methane formation and is more readily available under pressure for such purposes, methane-forming bacteria are especially sensitive to environmental changes. When carbon dioxide concentration begins to exceed the saturation level at 5 atmospheres, methane bacteria tend to be inhibited. This inhibition then becomes a limiting factor in operating pressures (tank construction cost is, of course, another limitation on operating pressures).

Table IV shows absorption factors at feasible operating pressures for various recirculation rates. Allowing for system operating efficiency (limited by recirculation of unsaturated sludge and incomplete degassification), an absorption factor of approximately 24 is required to produce high-quality methane in a well-operated system. Operating factors of 3 atmospheres and 7 recirculations may be nearly ideal in many cases.

TABLE IV

ABSORPTION FACTORS AT VARIOUS PRESSURES AND RECIRCULATION RATES

| Recirculation Rate[1] | Pressure Factor in Atmosphere[2] | | | | |
| --- | --- | --- | --- | --- | --- |
| | 1 | 2 | 3 | 4 | 5 |
| 2 | 3 | 6 | 9 | 12 | 15 |
| 3 | 4 | 8 | 12 | 16 | 20 |
| 4 | 5 | 10 | 15 | 20 | 25 |
| 5 | 6 | 12 | 18 | 24 | 30 |
| 6 | 7 | 14 | 21 | 28 | 35 |
| 7 | 8 | 16 | 24 | 32 | 40 |
| 8 | 9 | 18 | 27 | 36 | 45 |
| 9 | 10 | 20 | 30 | 40 | 50 |
| 10 | 11 | 22 | 33 | 44 | 55 |

[1]Recirculation rate is based upon feed volume. Feed volume is normally 0.2 gpm per 1000 cubic feet of methane production per day. A recirculation rate of 2 then would be 0.4 gpm per 1000 cubic feet of daily capacity. For the system of FIG. 1 the recirculation rate is (528 + 26)/(105 − 26) = 7 or [(X) + (XX)]/[(III) − (XX)].
[2]One atmosphere is assumed to be 14.7 pounds per square inch gauge, and total pressure is the sum of hydraulic head plus mechanical loading.

Table V lists the depressurization cycles for a system operated at various pressures and using the periodic depressurization configuration.

TABLE V

DEPRESSURIZATION CYCLES

| Pressure Factor (In Atmospheres, Gauge) | Approximate Depressurization Frequency (Hours) |
| --- | --- |
| 2 | 8 |
| 3 | 12 |
| 4 | 18 |
| 5 | 24 |

Table VI shows the power requirements for the various absorption factors in Table IV.

TABLE VI

POWER FACTORS FOR PUMPING

| | | KWH*/mcf at P | | | | |
| --- | --- | --- | --- | --- | --- | --- |
| R** | gpm/mcf | 1 ATM*** | 2 ATM | 3 ATM | 4 ATM | 5 ATM |
| 2 | 0.4 | 0.150 | 0.230 | 0.309 | 0.388 | 0.469 |
| 3 | 0.6 | 0.225 | 0.345 | 0.464 | 0.582 | 0.704 |
| 4 | 0.8 | 0.300 | 0.460 | 0.618 | 0.776 | 0.938 |
| 5 | 1.0 | 0.375 | 0.575 | 0.773 | 0.970 | 1.173 |
| 6 | 1.2 | 0.450 | 0.690 | 0.927 | 1.164 | 1.408 |
| 7 | 1.4 | 0.525 | 0.805 | 1.082 | 1.358 | 1.642 |
| 8 | 1.6 | 0.660 | 0.920 | 1.236 | 1.552 | 1.876 |
| 9 | 1.8 | 0.675 | 1.035 | 1.391 | 1.746 | 2.111 |
| 10 | 2.0 | 0.750 | 1.150 | 1.545 | 1.940 | 2.346 |

*Assumes a friction head of 30 feet.
**Recirculation Factor.
***1 ATM = 14.7 psig.

Power factors for the in-tank depressurization option are practically nil. When such a unit is built underground, only the cost of periodically draining the standpipe is incurred. Even at only 2 atmospheres of operating pressure and an 8 hour depressurization cycle, a maximum of 0.050 KWH per mcf is required.

Heating sludge approximately 6° C reduces carbon dioxide solubility by 13 percent. Changing heating practice (using higher temperatures) enhances efficiency somewhat.

When carbon dioxide vaporizes during stripping, there is a heat loss. At 35° C this heat loss (heat of vaporization) amounts to approximately 1.4 calories per gram (FIG. 1). When the sludge is repressurized and carbon dioxide forms, this loss is reversed by the condensation of carbon dioxide. Likewise, because carbon dioxide reacts with water to form carbonic acid, heat of solution is generated, but is reversed during degassification.

All other thermal balance considerations (conductive loss, heat of formation, etc.) are accounted for in standard digester design.

From the preceding description and with reference, e.g., to FIG. 1 it is appreciated that 231 cfm of methane are withdrawn from Stage 1 Digester and 115 cfm of methane are withdrawn from Stage 2 Digester without attendant $CO_2$ or $H_2S$ because the sludge in the several digesters is unsaturated with regard to both $CO_2$ and $H_2S$, whereas it is saturated with regard to methane. The methane thus precipitates and is released from the sludge in gaseous form. Carbon dioxide and hydrogen sulfide remain in solution (in the sludge) until pressure in the respective digesters is reduced. When pressure is reduced in the digesters, the equilibrium therein shifts, and the slugde becomes oversaturated with regard to $CO_2$ and $H_2S$; these gases then precipitate and are released from the sludge.

Methane is produced continuously during digestion; it precipitates and collects in the digester dome top. Thus produced and precipitated methane is discharged through a pressure relief valve which maintains digester operating pressure. Separation of methane thus occurs continuously as it is generated. Carbon dioxide and hydrogen sulfide separate from sludge only during depressurization, which is effected over a total of about twenty minutes for each 8-hour digestion period or about 4 percent of the time. During depressurization a small amount (at most 8 percent) of methane can be lost by recirculation through a degasser, as shown in FIG. 1.

Carbon dioxide is continuously generated during digestion and is absorbed by sludge at digestion pressure. It does not precipitate from sludge until the sludge is subjected to a pressure drop. It is alternatively removed from sludge by passing the latter through a degasser. Sludge from which carbon dioxide has been removed has an increased power of absorption for more carbon dioxide, and the cycle is repeated.

Exemplary embodiment of the present invention follow. These examples are presented solely for the purpose of illustration and in no way limit the nature or scope of the invention.

EXAMPLE 1

(Assuming climatic conditions comparable to Lubbock, Tex.) Seventy-eight pounds per minute (dry matter) of beef-cattle feedlot waste (I) are blended with water and thickened seed to a consistency of approximately 12 percent solids. (Manure may require grinding). This material (III) is continuously pumped (approximately 105 gpm) into an initial (Stage 1) digestion tank (IV) of 500,000 gallons capacity. This vertical cylindrical tank is 34 feet in side wall depth, 50 feet in diameter, and of steel construction capable of being operated continuously at 2.5 atmospheres (37 psig) of pressure. The tank is also completely mixed by a commercial unit designed for such service (i.e. Dorr-Oliver Dynamix). Sludge from this tank is continuously transferred (V) into a second (Stage 2) digester of equal specifications. This transfer includes not only the 105 gpm feed of sludge, but also 528 gpm of degassified and heated sludge. Total transfer from Stage 1 to Stage 2 digestion totals approximately 633 gpm.

From Stage 2, 633 gpm is continuously withdrawn (to balance inflow). Of this flow approximately 105 gpm (XIII) is directed to a flotation thickener. Fifty-three gallons per minute of this 105 gpm leaves the flotation unit as subnatant (XXI) and flows to a lagoon (XXIII) for treatment and subsequent recirculation. The remaining 52 gpm is split equally for sludge dewatering (XV) and for recycle (XX) to the Stage 1 digester.

Of the 633 gpm from Stage 2 the other 528 gpm is directed through the heating-degassing loop. In winter as much as 350 gpm may be put through the heater (VII) on an average in order to maintain a sludge temperature of approximately 35° C in the digesters. In summer much less heating is required and as little as 150 gpm average heater flow may be necessary. The entire 528 gpm, whether heated or not, is directed through the degasser unit (VIII) where carbon dioxide and minor amounts of hydrogen sulfide are stripped. The degasser operates at atmospheric pressure and employs a system of cascading cones to strip the acid gases from the sludge. An exhaust fan continuously removes the gas from the degasser. The multicone cascading system provides intimate exposure of sludge to warm air so that diffusion of carbon dioxide, hydrogen sulfide and a minor amount of methane is effected.

After degassing, the volume of 528 gpm (IX) is then pumped into the stage 1 digester and is thus repressurized. This operation yields approximately 500,000 cubic feet of methane per day [60 to 80% from Stage 1 (XI), the remainder from Stage 2 (X)]. Approximately 100,000 cubic feet is consumed within the system to provide energy for sludge heating (XII) and sludge drying (XXVIII). On an average 35,000 cubic feet may be used for sludge heating and 50,000 cubic feet for sludge drying.

A total of 63 gpm [from lagoon recycle plus make-up (XXVII) water] is then returned (XXIV) to the blender for mixing with the 78 pounds per minute of manure (dry basis) to close the loop.

After dewatering (XVI) to less than 40 percent moisture, the thickened sludge is dried (XVIII) in, e.g., a flash drying unit to produce a marketable product (XIX). Sludge production averages approximately 25 toms per day or half of the manure feed tonnage.

EXAMPLE 2

Seventy-eight pounds per minute (dry matter) of beef-cattle feedlot wastes are blended with water and seed recycle to a consistency of approximately twelve percent solids. This material is continuously pumped (approximately 105 gpm) into an initial (Stage 1) digestion tank of approximately 500,000 gallons capacity. This tank is located approximately 78 feet underground, is 34 feet in sidewall depth and is 50 feet in diameter. Construction is of a one-fourth inch inner steel liner set in concrete. Offset from the tank, but hydraulically connected, is a standpipe which is four feet in diameter and extends approximately 44 feet above the ground surface. This tank is completely mixed and heated to 35° C by commercial units designed for such service. Pressure on the tank is maintained by keeping the standpipe filled with water.

Sludge from this tank is continuously transferred into a second (Stage 2) digester of identical specifications. Both tanks are depressurized approximately every 12 hours for 15 minutes by pumping water from the standpipes until a water level equal to the sludge level in the digesters is reached. Gas produced during this degassing step is wasted to the atmosphere.

From Stage 2 sludge is continuously withdrawn and directed to a flotation thickener. A total of 105 gpm is treated in the thickener with 53 gpm coming off as subnatant and 52 gpm as thickened sludge. One-half of the thickened sludge is then dewatered and dried while the other one-half is recirculated into Stage 1 as seed. All other operating parameters and production are similar to those of Example 1.

The system (for either Example 1 or Example 2) can readily be modified in numerous ways. For example, degassed sludge (IX) can be combined with blender feed (XX) rather than being directly recycled into the stage 1 digester. Alternatively, it can be combined with blended feed (III). Likewise, thickened sludge (XX) can be preliminarily combined with feed water (XXIV). The depicted configurations are preferred.

The invention and its advantages are readily understood from the foregoing description. Various changes are apparent without departing from the spirit and scope of the invention or sacrificing its material advantages.

What is claimed is:

1. In anaerobic digestion of organic solid waste to produce methane gas in a digester, the improvement wherein the digestion is effected, so that gas in the digester is under a pressure of at least one atmosphere in excess of atmospheric pressure so that digesting organic solid waste preferentially absorbs carbon dioxide.

2. A process according to claim 1 wherein the pressure is within the range of from about two atmospheres to about 5 atmospheres gauge.

3. A process according to claim 2 having a daily feed volume and a recirculation rate of from 4 to 10 times the daily feed volume.

4. A process according to claim 1 which comprises anaerobically digesting solid waste at a pressure of at least 14.7 psig, depressurizing obtained pressurized sludge, heating digested and depressurized sludge, recycling digested and depressurized sludge to the digesting organic solid waste, partially dewatering digested and depressurized sludge, combining digested and depressurized sludge with organic solid waste and water, and introducing a combination of (a) digested and depressurized sludge, (b) organic solid waste and (c) water into the digesting organic solid waste.

5. A process for increasing carbon dioxide availability as a hydrogen acceptor for biological methane gas formation which comprises anaerobic digestion according to claim 1.

6. A process for facilitating flotation thickening of digested sludge which comprises anaerobic digestion according to claim 1 and release of the pressure under which the sludge was digested.

7. A process according to claim 1 which comprises recirculation of temporarily-depressurized digested sludge.

8. A process according to claim 1 which further comprises stripping or scrubbing acid gases from sludge produced by the anaerobic digestion by temporarily depressurizing the sludge and then recirculating it to the digestion under pressure.

9. A process according to claim 1 which further comprises stripping or scrubbing carbon dioxide and hydrogen sulfide from sludge produced by the anaerobic digestion by temporarily depressurizing the sludge and recirculating it to the digestion under pressure.

10. A process for maintaining digesting sludge in an unsaturated state with regard to carbon dioxide concentration which comprises temporarily depressurizing sludge produced by anaerobic digestion according to claim 1 and recirculating resulting depressurized sludge to the digestion under pressure.

11. A process for producing high-quality methane gas which comprises anaerobic digestion according to claim 1 and recirculation of temporarily-depressurized digested sludge.

12. A process according to claim 1 which comprises temporarily depressurizing digested sludge, heating the resulting depressurized sludge, stripping comprised gas from thus-obtained heated sludge and recirculating thus-produced stripped sludge to the digestion under pressure.

13. A process for improving the quality of methane produced according to claim 1 which comprises temporarily depressurizing during said digestion.

14. A process according to claim 13 which comprises periodically depressurizing during said digestion.

15. A process according to calim 1 wherein the pressure is maintained hydrostatically.

16. Anaerobic digestion according to claim 1 wherein the organic solid waste is manure and which comprises producing about 0.5 pound of digested sludge having less than 10 percent by weight of water and in excess of about 3.5 cubic feet of high-quality methane gas at a pressure of 800 psig per pound of dry manure feed.

17. A process according to claim 16 wherein the high-quality methane gas is at least about 98 percent methane.

* * * * *